(12) United States Patent
Tyler

(10) Patent No.: US 9,592,153 B2
(45) Date of Patent: Mar. 14, 2017

(54) DEVICES AND METHOD FOR TREATING GLAUCOMA

(71) Applicant: Thomas D. Tyler, San Carlos, CA (US)

(72) Inventor: Thomas D. Tyler, San Carlos, CA (US)

(*) Notice: Subject to any disclaimer, the term of this patent is extended or adjusted under 35 U.S.C. 154(b) by 231 days.

(21) Appl. No.: 14/645,115

(22) Filed: Mar. 11, 2015

(65) Prior Publication Data
US 2015/0320598 A1    Nov. 12, 2015

Related U.S. Application Data

(60) Provisional application No. 61/990,871, filed on May 9, 2014.

(51) Int. Cl.
*A61F 9/007*    (2006.01)

(52) U.S. Cl.
CPC .. *A61F 9/00781* (2013.01); *A61F 2210/0014* (2013.01); *A61F 2210/0023* (2013.01); *A61F 2210/0076* (2013.01); *A61F 2230/0013* (2013.01)

(58) Field of Classification Search
CPC ...... A61F 2/147; A61F 9/0008; A61F 9/0017; A61F 9/00781; A61F 2210/0014; A61F 2210/0023; A61F 2210/0076; A61F 2230/0013; A61F 2230/0015; A61M 27/002

See application file for complete search history.

(56) References Cited

U.S. PATENT DOCUMENTS

2014/0277051 A1*    9/2014    Schachar ............ A61F 9/00781
                                                        606/185

* cited by examiner

*Primary Examiner* — Todd J Scherbel
(74) *Attorney, Agent, or Firm* — Sheppard, Mullin, Richter & Hampton LLP

(57) ABSTRACT

A method is described for treating glaucoma by surgically implanting a shape recoverable member in the sclera of the eye. The shape recovery member is adapted to recover involutely when shape recovery is caused to occur. The bending of the shape recoverable member during its recovery exerts pressure on longitudinal ciliary muscle to supply tension to and open the trabecular meshwork. As a result, aqueous humor flows more freely and reduces the intraocular pressure.

20 Claims, 4 Drawing Sheets

DEVICES AND METHOD FOR TREATING GLAUCOMA

This application claims the benefit of U.S. Provisional Application No. 61/990,871 filed May 9, 2014, which is hereby incorporated herein by reference in its entirety.

BACKGROUND OF THE INVENTION

1. Field of the Invention

The present invention is generally directed to a surgical method for treating glaucoma, and relates more particularly to a method for mechanically altering the insertion angle between the longitudinal ciliary muscle and the scleral spur causing the scleral spur to apply greater tension to the trabecular meshwork thereby opening the meshwork to reduce resistance to outflow of the aqueous humor from the anterior of the eye, thus reducing intraocular pressure.

2. Description of the Prior Art

Glaucoma is a significant public health problem, because it is a major cause of blindness that involves both the central and peripheral vision. Glaucoma is a form of optic neuropathy (a disorder of the optic nerve) that is associated with an increase in intraocular pressure resulting from the eye lacking the ability to relieve the pressure in the anterior chamber of the eye caused by an abnormal buildup in the anterior of the clear fluid known as "aqueous humor." Aqueous humor, which is formed in the ciliary body in the posterior chamber of the eye at the rate of about 2.5 microliters per minute, enters the anterior chamber through a cleft between the front of the lens and the back of the iris through the pupillary opening in the iris. When the eye is functioning normally, the aqueous humor flows out of the anterior chamber at the same or substantially the same rate it enters and, as result, the pressure in the eye remains safely within the normal range of about 12 to 22 mmHg.

Outflow of aqueous humor from the anterior chamber is by two routes. A minor amount (about 10%) exits through "uveoscleral drainage" between muscle fibers in the ciliary body. This flow is independent of intraocular pressure. However, the major route of outflow is through the trabecular meshwork into Schlemm's canal and is pressure dependent. When this route becomes impeded, the intraocular pressure can become elevated because the inflow of aqueous humor is not balanced until the pressure in the eye rises sufficiently to overcome the impediment to outflow. The result of this increase in pressure is that the pressure is transmitted to the vitreous body which, in turn, presses the retina against the choroid which compresses the blood vessels that feed the retina. In time this can result in loss of vision, both peripheral and central, and eventually lead to complete blindness.

Raised intraocular pressure is the most important and the only clinically modifiable risk factor for glaucoma currently available. The clinical treatment of glaucoma is typically approached in a step-wise fashion. Medication often is the first treatment option. Administered either topically, the most common approach, or sometimes orally, the medications used to treat glaucoma work to either reduce aqueous production or to increase outflow. Currently available medications have many serious side effects including: congestive heart failure, respiratory distress, hypertension, depression, renal stones, aplastic anemia, sexual dysfunction and death. Compliance with medication is also a major problem, with some estimates that over half of glaucoma patients do not follow their correct dosing schedules. In one study by an HMO, half of patients surveyed did not fill the prescription the first time and one-fourth failed to do so the second time. Compliance is also complicated by the fact that, in the early stages at least, patients with glaucoma may be asymptomatic.

When medication fails to adequately reduce the pressure, a variety of surgical techniques can be employed. Generally these include canaloplasty, laser trabeculoplasty, trabeculectomy, and the insertion of shunts. Generally these surgical interventions provide only temporary relief from elevated intraocular pressure and disease progression can resume. Accordingly there remains a substantial need for improved treatments for glaucoma, particular ones that are not medication regimens requiring strict patient compliance or surgical techniques that are only temporarily successful.

SUMMARY OF THE INVENTION

The present invention is directed to a novel surgical method for the treatment of glaucoma in which a shape recoverable device in a first configuration is implanted in the sclera of the eye adjacent to the longitudinal ciliary muscle. After implantation, the shape recoverable device is caused to recover from the first configuration in which it was inserted to a second configuration in which it exerts lateral pressure on the longitudinal ciliary muscle. The pressure exerted by this shape change alters the insertion angle between the longitudinal ciliary muscle and the spur of the sclera which enhances the force with which the scleral spur applies tension to the trabecular meshwork. This results in opening of the trabecular meshwork which allows the aqueous humor to flow more freely through the meshwork and into Schlemm's canal with a concomitant reduction in intraocular pressure within the eye.

In a preferred embodiment of the invention, the shape recoverable member is a member that recovers from a relatively flat, planar (or slightly curved) first configuration involutely to a curved second configuration wherein the bending from the flat, or slightly curved shape to the curved configuration advances the curved portion of the member into closer proximity to the longitudinal ciliary muscle resulting in the application of lateral pressure on the muscle. Further, the shape recoverable member is preferably a heat recoverable member wherein the shape recovery is caused by the application of thermal energy to the shape recoverable member.

As noted above, a property of the shape recoverable member is the ability to "curl" in involute fashion when recovering from the first to the second configuration. When the shape recoverable member is a heat recoverable member, it will typically have a laminar construction comprised of at first and second lamina. The first lamina of the bilayer is a unidirectionally expanded member in its first configuration which, unless restrained, will contract or shrink to its unexpanded dimensions when heated above a temperature, its "recovery temperature," at which, unless restrained, return to the configuration from which it was expanded. When the lamina is fabricated from a polymeric material this temperature is or at least functions like its "melting point." The second lamina is a flexible member which, in the case of a lamina fabricated from a polymeric material has a higher melting point (and often a lower melt index) than the first member and tends to restrain the first member from returning to its original configuration when heat is applied. As a result, the laminate bilayer "curls" when heat is applied because of the combination of recovery of the first lamina and the restraint on its recovery to its original shape by the second lamina. Optionally, the laminate can include a third "barrier" layer to assist in dissipating the energy applied to the device to cause recovery from the first configuration to the second configuration.

According to the invention, the shape recoverable member is implanted into the sclera adjacent to the longitudinal ciliary muscle in an orientation in which involute recovery advances the curl induced into the member by involute shape recovery in a manner which causes the shape recoverable to exert lateral pressure on the longitudinal ciliary muscle. When the member is a heat recoverable member, after implantation thermal energy is applied to the heat recoverable member to cause it warm to a temperature which is at or above its recovery temperature at which it will attempt to recover from the first to the second configuration. Desirably, full shape recovery of the heat recoverable member will not be necessary in order to achieve the desired reduction in intraocular pressure in the eye. Accordingly, the duration of the application of heat can, and usually will be, less than the time required for full shape recovery.

Thus, after the application of energy to cause shape recovery, the intraocular pressure of the eye is measured. If the measurement indicates that the reduction in intraocular pressure has not resulted in a pressure deemed safe, additional energy can be applied to cause further shape recovery until the desired result is achieved. Furthermore, if subsequent to the original implantation monitoring of the patient's intraocular pressure reveals that the intraocular pressure has risen again to an unsafe level, thermal energy can be reapplied to cause further recovery of the residual recovery retained by the heat recoverable member without the necessity of doing additional surgery.

DETAILED DESCRIPTION OF THE PREFERRED EMBODIMENTS

Figure 1:
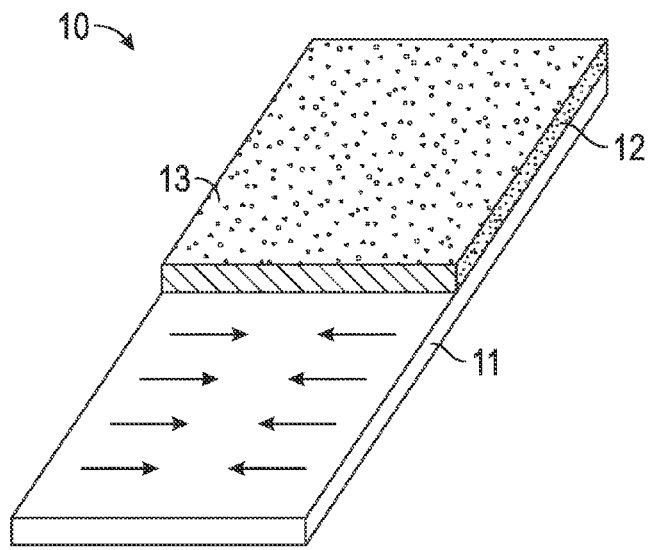
FIG. 1 is a perspective view, partially in cross-section, of a laminar shape recoverable member.
Figure 2:
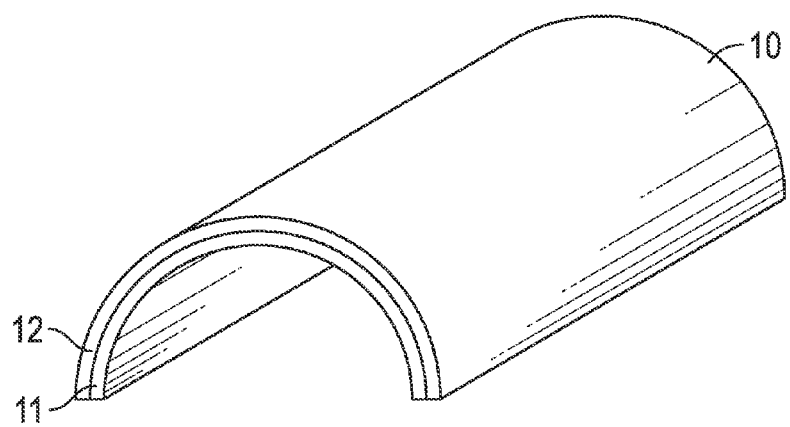
FIG. 2 is a perspective view of the laminar shape recoverable member of FIG. 1 after shape recovery has been caused to occur.
Figure 3:
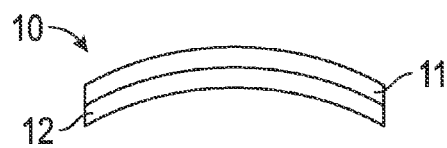
FIG. 3 is a lateral view of a preferred shape recoverable member useful in the invention.

Turning now to the figures, FIG. 1 illustrates a laminar heat recoverable member 10 useful in the method of the present invention. Layer or lamina 11 of member 10 is a heat recoverable lamina which has been expanded unidirectionally in a direction opposite the arrows, but which will tend to recover in the direction of the arrows when heated above its recovery temperature. Lamina or layer 12 is, in the broadest sense, a lamina comprised of a material that tends to restrain the recovery of layer 11 to the dimensions it possessed prior to unidirectional expansion. Thus, when the laminate is heated to the point at which layer 11 begins to recover, the combination of recovery of layer 11 opposed by the resistance of layer 12 produces the involute recovery illustrated in FIG. 2. A detailed description of a process for making such an article can be found in U.S. Pat. No. 3,899,807, the disclosure of which is incorporated herein by reference. In a particularly preferred embodiment of the invention, a slightly curved or arcuate shape is imparted to the member 10 of FIG. 1 prior to implantation in the eye is illustrated in FIG. 3. It should be noted that this curvature, which is selected to approximate that of the sclera of the eye in which it is to be implanted, is in a direction which is opposite the direction of recovery after implantation.

In a typical construction of heat recoverable member 10, layer 11 comprises a suitable unidirectionally expanded heat shrinkable polymeric material and layer 12 is comprised of a non-heat shrinkable polymeric having a higher melting point than layer 11. As used herein, the term "melting point" is not to be interpreted as meaning the temperature at which the material of layer 11 actually flows. Typically heat recoverable polymers are cross linked polymers that have crystalline properties below their melting point and elastomeric properties above the melting point. Crosslinking prevents the polymer from becoming sufficiently fluid to permit it to actually flow, however. Thus, the term melting point refers to the temperature or temperature range at which the crystalline properties are lost and the polymer exhibits elastomeric properties which permit it to be readily deformed. When using such polymeric materials to make a heat recoverable member, the polymeric material is fabricated to give it a shape to which recovery is desired and then heated above its crystalline melting point at which it can be readily deformed to a configuration from which recovery is desired and maintained in that shape until its temperature is lowered again to below the crystalline melting point. Non-crystalline polymeric materials can be similarly manipulated in appropriate cases by manipulating them above and below their glass transition temperatures. The manipulation of crystalline polymers and polymers with glass transition points to make heat recoverable members by exploiting these properties is explained in more detail in U.S. Pat. No. 3,899,807. Most commonly, the layers 11 and 12 of member 10 are assembled after unidirectional expansion of layer 11 to form the laminate of FIG. 1. A number of suitable techniques of making laminar heat recoverable articles that undergo involute shape change from polymers with crystalline melting points or glass transition temperatures are described in aforementioned U.S. Pat. No. 3,899,807.

Because layers 11 and 12 of member 10 are fabricated of flexible materials, they can be curved or bent slightly before being joined to form laminar member 10 to impart a curved or arcuate shape as shown in FIG. 3. The laminae 11 and 12 of shape recoverable member 10 can be bonded together to form a unitary structure using, for example and depending on the materials being joined, adhesives, pressure, or the application of solvents to the surfaces being joined.

Shrinkable layer 11 is preferably formed of a low melting point, non-toxic material which is heat-shrinkable material so that shape recovery can be caused to occur at a temperature which is not dangerous to the eye. Thus, Layer 11 should be formed of a material having a melting point of less than about 100° C., preferably from about 45-60° C., and more preferably from about 50-55° C. In some embodiments, layer 11 should be formed of a material having a melt index of at least about 4.5 g/10 min., preferably from about 63-260 g/10 min., and more preferably from about 6.3-15.0 g/10 min. (at an extrusion pressure of 2.16 kg and a temperature of 190° C. as defined by ASTM D-1238). A particularly preferred material for use as layer 11 is a polymethylmethacrylate (PMMA) or a mixture of polymethylmethacrylates wherein the polymethylmethacrylate or mixture thereof has the described melting point and/or melt index. A particularly preferred polymethylmethacrylate for use as shrinking layer 34 is sold under the name ICI 924 CL (available from ICI Acrylics, Inc.).

Restraining layer 12 is preferably formed of a higher melting point, non-toxic material which is bendable, but will not readily shrink upon the heat application require to cause shape recovery of layer 11. Thus, restraining layer 12 should be formed of a material having a melting point that is at least about 5° higher, preferably at least about 10° higher, and more preferably 20°-30° higher than the melting point of layer 11. Suitable materials will typically exhibit a melting point that is at least about 50° C. and preferably from about 60-100° C., and more preferably from about 70-80° C. In some embodiments, layer 12 should be formed of a material having a melt index of less than about 4.4 g/10 min., preferably from about 1.1-4.4 g/10 min., and more preferably from about 1.1-2.2 g/10 min (at an extrusion pressure of 2.1 6 kg and a temperature of 190° C. as defined by ASTM D-1238). Similar to shrinkable layer 11, a particularly preferred material for use as restraining layer 12 is a polymethylmethacrylate or a mixture of polymethylmethacrylates wherein the polymethylmethacrylate or mixture thereof has the described melting point and/or melt index. A particularly preferred polymethylmethacrylate for use as restraining layer 12 is sold under the name ICI 1000 ECL (available from ICI Acrylics, Inc.).

In another embodiment, the ASTM D-1238 melt index of shrinkable layer 11 is at least about 2 times, preferably at least about 4 times, and more preferably from about 6-26 times greater than the ASTM D-1238 melt index of restraining layer 12.

Other types of materials (both synthetic and natural resins as well as plastics formed from these resins) can be utilized to form heat shrinkable layer 11 or restraining layer 12. Other suitable synthetic resins include polyethylene, polypropylene, polyvinyl chloride, and polytetrafluorethylene. Shape memory materials including alloy, ceramic, polymers and gels might be utilized to form either layer 11 or layer 12.

Persons skilled in the art will appreciate that other heat recoverable structures can be utilized in the present invention. For example, a structure which is a member comprised of a single layer of a polymer, typically a crosslinked polymer, having a crystalline melting point above which it exhibits the properties of an elastomer and below which it is rigid, can be used. In such a case, the member is formed in the shape to which it is intended to recover, for example, the shape in FIG. 2, and then heated to a temperature above the crystalline melting point at which it is deformed to a shape like that of FIG. 3. After implantation and the application of heat, such a monolithic member would tend to recover from its deformed shape toward its original configuration in the same manner as the laminate structure described above.

Also multiple component polymers can produce a multiple shape memory polymer with multiple transitions (including glass transition and melting) (an intermediate shape between a temporary shape and the original shape). It may also be desirable to incorporate certain agents into the layers, to impart desired physical properties. Such agents include physiologically acceptable metals (e.g., zinc, gold, platinum, tantalum, stainless steel), ceramics, carbon, porcelain, alumina, silica, silicon carbide, glass). These incorporated agents such as carbon fibers, carbon nanotubules, iron oxide (III) in silicon matrix have inherent properties that when blended into shape memory materials can be used to activate the shape memory material with a variety of transition triggers including but not limited to thermal, photo, magnetic, electric stimuli and other radiofrequency devices.

It will be appreciated that the melting point of either heat shrinkable layer 11 and/or restraining layer 12 can be modified by the addition of a compound to alter the melting point of the particular layer. Examples of such compounds include carbon black, indocyanine green, methylene blue, zinc oxide, because they preferentially absorb energy at certain energy wavelengths. In particularly preferred embodiments, shrinking layer 11 is formed of a material which comprises from about 0.1-2.0% by weight zinc oxide, and preferably from about 0.25-0.75% by weight zinc oxide, based upon the total weight of the material taken as 100% by weight. Of course, those skilled in the art will appreciate that the type and quantity of energy-absorbing dye utilized can be altered depending upon the desired application.

The member 10 can also be formed by co-extruding the materials of which the respective layers are formed rather than being formed by bonding the layers together through solvents, pressure, or other physical methods. Techniques for forming heat recoverable laminates based on coextruded materials are described in WO2013/159102, the disclosure of which is incorporated herein by reference. Regardless, layers 11 and 12 will be bonded to one at the surfaces defining their length and width to form member 10.

A barrier layer (not shown) can also be applied to the outer surface 13 of heat shrinkable layer 11 to protect the tissue adjacent layer 11 from damage during heating thereof. The barrier layer should also be formed of a high melting point, bendable material such as those described with respect to restraining layer 12.

In the embodiment depicted, heat shrinkable layer 11 has a thickness of from about 0.125-1.50 mm, and preferably from about 0.125-0.75 mm, while restraining layer 12 has a thickness of from about 0.125-1.50 mm, and preferably from about 0.250-1.00 mm. Furthermore, the width of the member 10 at its widest point is from about 1.0-4.0 mm, and preferably from about 1.5-3.0 mm. In embodiments where member 10 is curved, the radius of curvature should be from about 7-10 mm so that the curve is substantially similar to the curvature of most human sclera at the site of device placement. Finally, it is preferred that the length of member 10 at its respective longest point is such that the member 10 can fit into a scleral pocket surgically formed adjacent the longitudinal ciliary muscle to receive it having a length of from about 3-8 mm, and preferably about 4.5 mm.

Although the invention is described and illustrated using a single shape recoverable member, typically plural shape recoverable members will be implanted at different locations within the sclera spaced relative uniformly apart from each other. Preferably, in a typical procedure to lower intraocular pressure at least one shape recoverable members 10 will be used, and more preferable four shape recoverable members used. Those skilled in the art will appreciate that, in appropriate cases, even more than four shape recoverable members can be used.

After the desired number of shaped recoverable members 10 are implanted and exposed to energy that causes them to undergo shape recovery, the intraocular pressure of the eye is measured according to known methods (e.g., by measuring the applanation pressure). The source of energy is not critical, so long as it can be applied with sufficient intensity to cause layer 11 to shrink or contract. At the same time, the energy should be provided with a sufficiently low intensity so as to minimize, and preferably prevent, layer 12 from melting or shrinking as well as to avoid damage to the eye tissue surrounding the shape recoverable member 10.

Types of energy sources which can be utilized include UV sources, magnetic fields, IR sources, radio frequency emitters, heat, and electrical, including low voltage DC and low voltage high frequency sources. However, the most preferred energy source is a laser 14 of the type typically utilized by an ophthalmologic surgeon. The identity, intensity, and duration of the application of the laser used to adjust the shape of shape recoverable member 10 can be readily selected by a person of ordinary skill in the art. Preferred lasers include diode IR (which have a wavelength of about 8104 nm) and argon (argon blue which has a wavelength of about 488 nm, argon green which has a wavelength of about 514.5 nm, or a combination of the two) lasers. However, any of the following lasers can be used as well: carbon dioxide; helium-neon; helium-cadmium; argon ion; krypton ion; xenon ion; nitrous oxide; iodine; holmium-doped yttrium-aluminum garnet; yttrium lithium fluoride; excimer; chemical; harmonically oscillated; dye; nitrogen; neodymium; erbium; ruby; and titanium-sapphire. With any of these types of lasers, the duration of treatment is typically from about 0.5-5.0 seconds while focusing on a location having a diameter of from about 300-500 μm.

If, after the initial energy treatment, the intraocular pressure remains above the target level, additional energy is applied as described above, and the intraocular pressure again measured with these steps being repeated as needed until the desired reduction in intraocular pressure is achieved.

Figure 4:
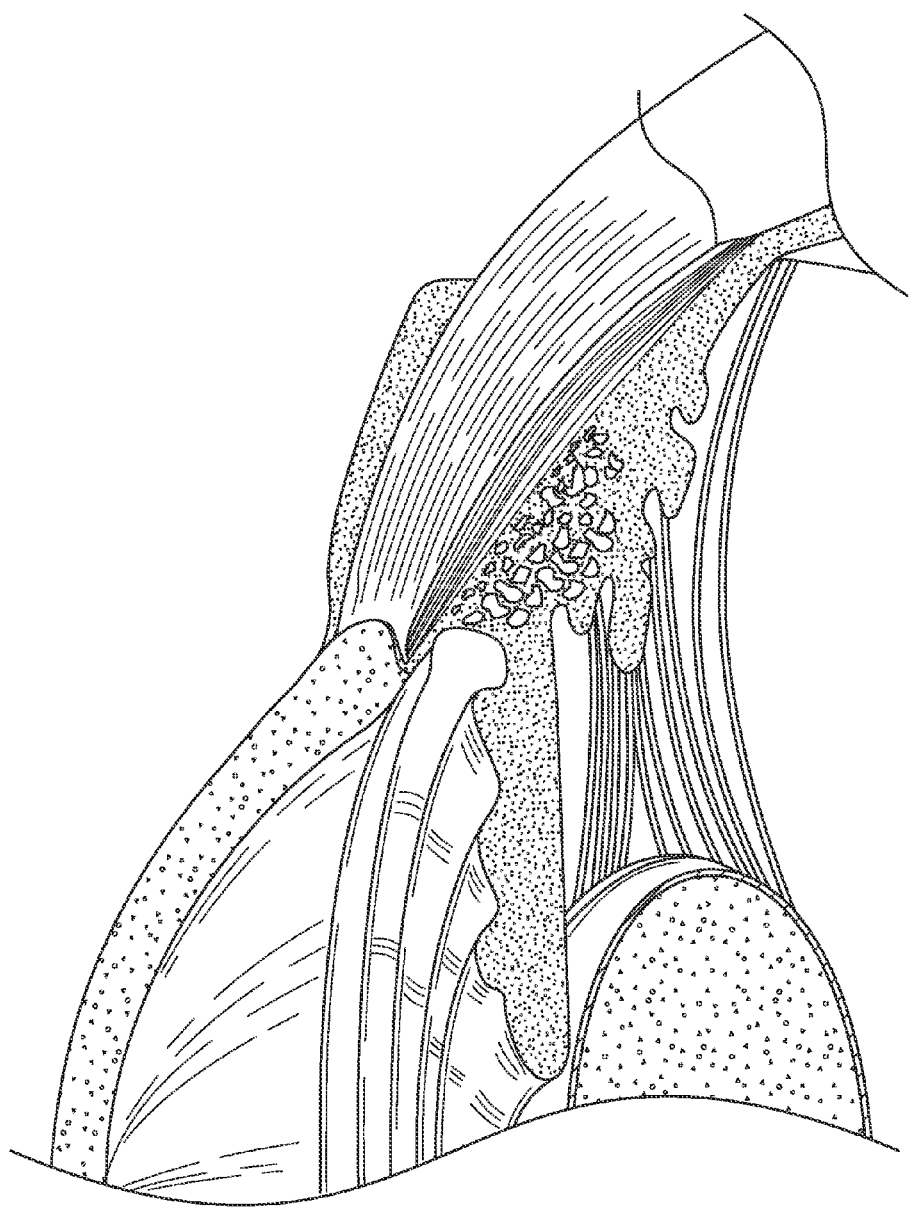
FIG. 4 is an illustration in cross-section showing certain anatomical details of the human eye before performance of the method of the present invention.
Figure 5:
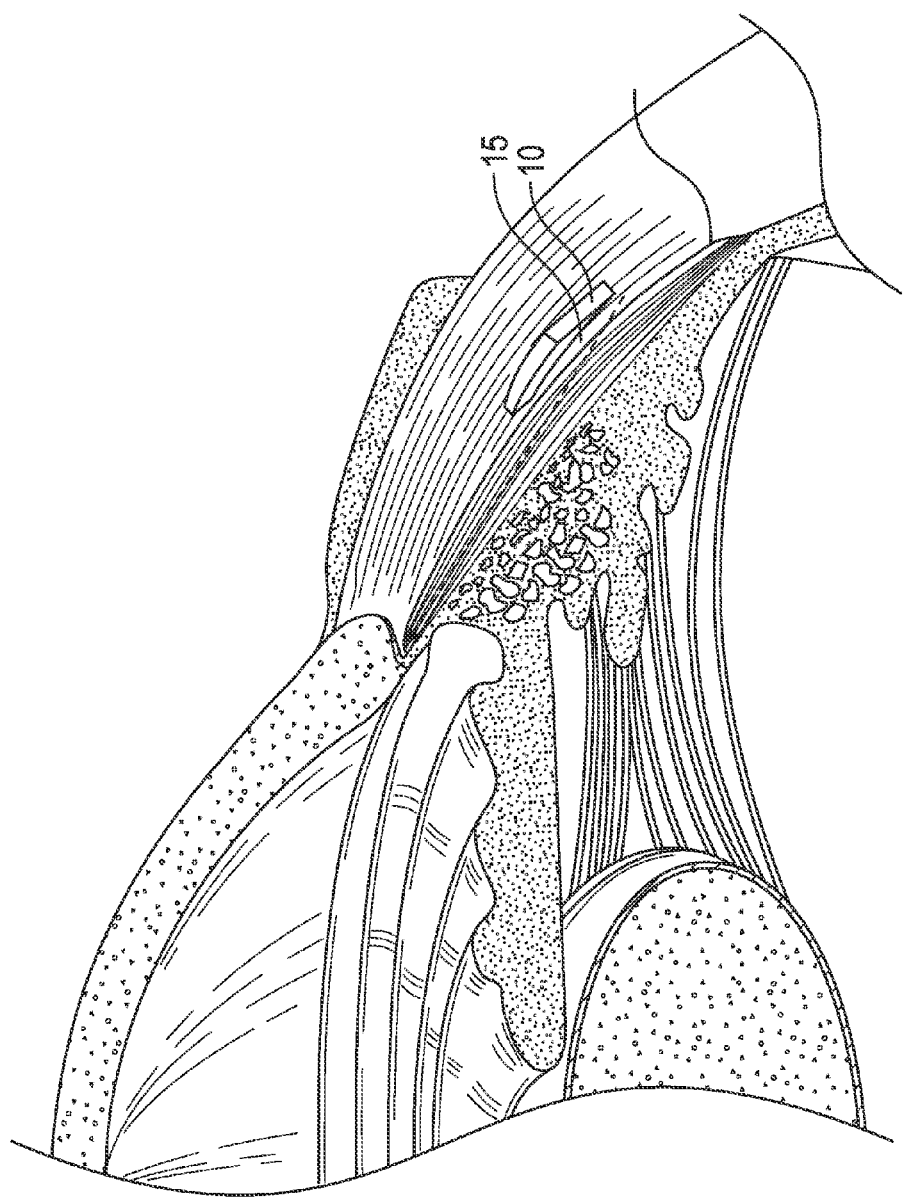
FIG. 5 is an illustration in cross-section of the human eye illustrating the position of a shape recoverable member after implantation according to the present invention.
Figure 6:
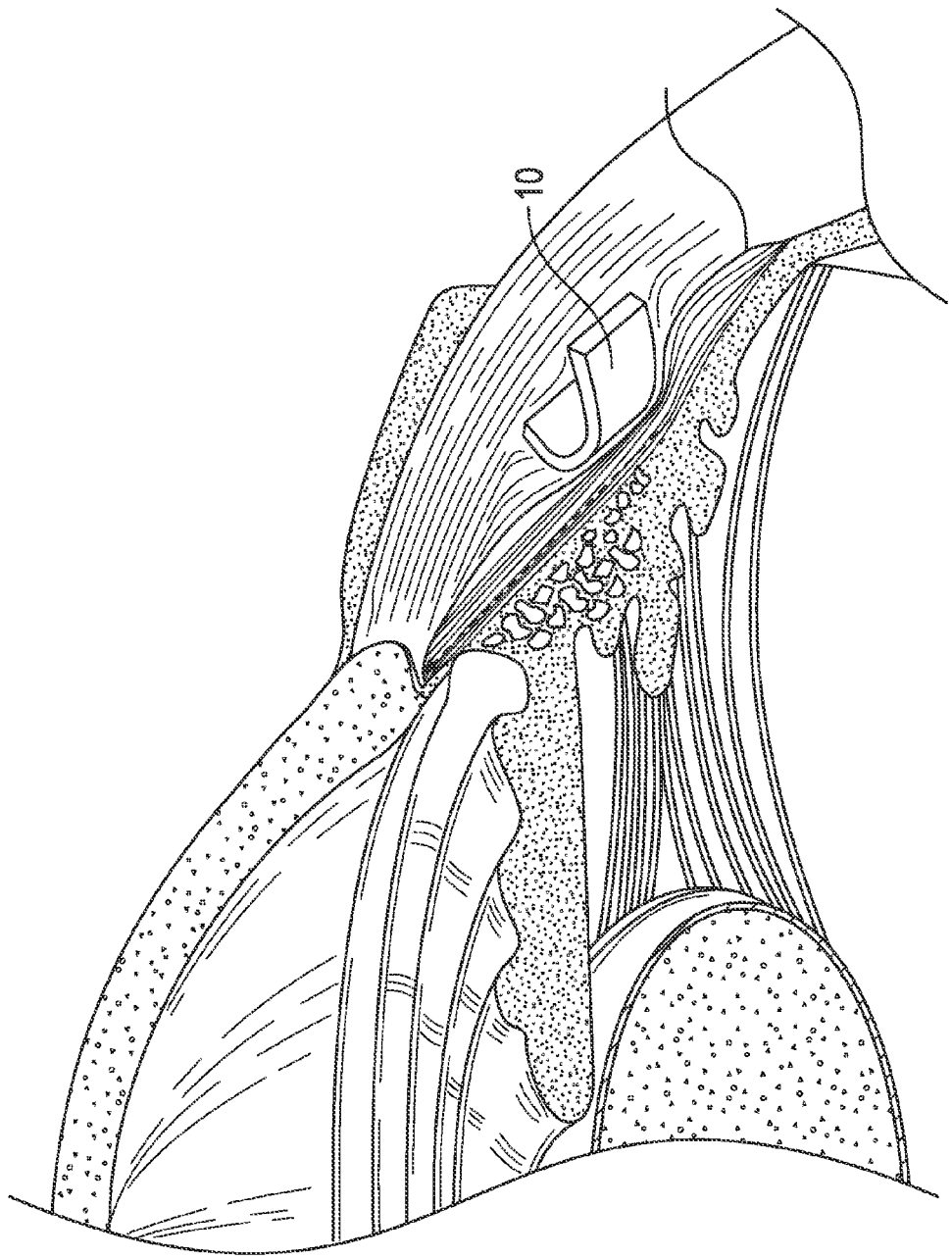
FIG. 6 is an illustration in cross-section of the human eye illustrating the effect of causing shape recovery of the shape recoverable member on the longitudinal ciliary muscle after implantation according to the present invention.

Referring to FIGS. 4-6, FIG. 4 is an illustration of a cross section of the eye with important anatomical elements identified. FIG. 5 is a similar illustration of the eye showing the proper location of shape recoverable member 10 in a scleral pocket 15 formed to receive it. Referring next to FIG. 6, an illustration of the eye similar to that of FIGS. 4 and 5, shape recoverable member 10 is shown after the application of energy to cause shape recovery and illustrates the result off exerting pressure on the longitudinal ciliary muscle. Thus, as the member 10 bends under the restraining force exerted by layer 12 on layer 11, it can alter the insertion angle between the scleral spur and the longitudinal ciliary muscle to cause the scleral spur to apply greater tension to the trabecular meshwork to open the trabecular meshwork and allow aqueous humor to flow more freely thereby reducing the intraocular pressure.

It will be appreciated that substantially the same result as that shown in FIG. 6 can be achieved by inverting member 10 in which case the ends of the shape recoverable member would recover toward the interior of the eye rather than the center portion. It will also be appreciated that, in such a case, the arcuate structure given member 10 to approximate the shape of the sclera of the eye would be in the opposite direction from that shown in FIG. 3.

Advantageously, unlike prior art devices, devices according to the instant invention can be adjusted after placement thereof in the sclera without subjecting the patient to further surgery. Thus, should the glaucoma condition worsen over time (e.g., about 2 years to 10 years after insertion), the patient can return to the surgeon who inserted the device, or to any other surgeon with an available energy-applying apparatus, and have the device further adjusted until acceptable accommodative intraocular pressure levels are achieved.

It will be appreciated that in some applications direct application of energy to layer 11 may create problems (e.g., pitting, bubbling, or irregular melting of the heat shrinkable layer 11). In these instances, it is generally desirable to apply the energy to bending layer 12, allowing it to be an energy source for the less tolerant shrinkable layer 11. This allows for a more uniform heat dispersion along and through shrinkable layer 11, thus minimizing or avoiding problems with the material of shrinking layer 11 as well as minimizing or substantially preventing damage to the surrounding tissue.

The potential amount of shrinkage available to shrinkable layer 11 will be determined during manufacturing by the extent of the stretching or pulling of the material of which shrinking layer 11 is formed prior to cooling and hardening. Additionally, the shrinkage can be controlled by the selection of the melt index of the material.

While the invention has been discussed with respect to the use of a generally rectangular, slightly curved shape recoverable member 10 for treatment of glaucoma, it should be understood that the invention is not so limited. For example, the size and shape of member 10 can be altered depending upon the shape and location of the area of the sclera in which it will be implanted.

While the invention has been described in detail by reference to the use of heat shrinkable members as the shape recoverable member of the invention. Those skilled in the art will appreciate that, as noted above, materials that undergo shape recovery upon the application of other than thermal energy can be used in the invention. For example, member 10 can be fabricated of a laminate in which layer 11 is a light-activated shape-memory polymer which is switched between being a rigid polymer and an elastomer by the application of UV light of different wavelengths.

The invention claimed is:

1. A method of treating an eye having a pathologic intraocular pressure resulting from glaucoma comprising the steps of:
   (i) implanting in the sclera of the eye adjacent to the longitudinal ciliary muscle an energy responsive shape recoverable member capable of adjustably recovering from a first configuration to a second configuration, said energy responsive shape recoverable member in said second configuration configured to exert a lateral, compressive pressure on the longitudinal ciliary muscle;
   (ii) causing the shape recoverable member to recover from the first configuration to the second configuration to exert said pressure on the longitudinal ciliary muscle;
   (iii) whereby the exertion of said pressure alters the insertion angle between the longitudinal ciliary muscle and the scleral spur causing the scleral spur to apply tension to and open the trabecular meshwork thereby allowing aqueous humor to flow more freely and reducing the intraocular pressure.

2. A method according to claim 1 wherein the shape recoverable member is a heat recoverable member.

3. A method according to claim 1 wherein the shape recoverable member is arcuate in its first configuration having a radius of curvature approximating the radius of curvature of the sclera.

4. A method according to claim 1 wherein the shape recoverable member recovers from the first to the second configuration involutely.

5. A method according to claim 1 wherein the shape recoverable member is implanted in a surgically generated scleral sac.

6. A method according to claim 1 wherein a plurality of shape recoverable members are implanted.

7. A method according to claim 6 wherein at least four shape recoverable members are inserted.

8. A method according to claim 7 wherein the shape recoverable members are heat recoverable members.

9. A method according to claim 1 wherein the shape recoverable member is a heat recoverable member.

10. A method of treating an eye having a pathologic intraocular pressure resulting from glaucoma comprising the steps of:
(i) implanting in the sclera of the eye adjacent to the longitudinal ciliary muscle a heat recoverable member capable of adjustably recovering from a first configuration to a second configuration, said heat recoverable member in said second configuration configured to exert a lateral, compressive pressure on the longitudinal ciliary muscle;
(ii) causing the heat recoverable member to recover from the first configuration to the second configuration to exert said pressure on the longitudinal ciliary muscle;
(iii) whereby the exertion of said pressure alters the insertion angle between the longitudinal ciliary muscle and the scleral spur causing the scleral spur to apply tension to and open the trabecular meshwork thereby allowing aqueous humor to flow more freely and reducing the intraocular pressure.

11. A method according to claim 10 wherein the heat recoverable member is arcuate in its first configuration having a radius of curvature approximating the radius of curvature of the sclera.

12. A method according to claim 10 wherein the heat recoverable member recovers from the first to the second configuration involutely.

13. A method according to claim 10 wherein the heat recoverable member is implanted in a surgically generated scleral sac.

14. A method according to claim 10 wherein a plurality of heat recoverable members are implanted.

15. A method according to claim 10 wherein at least four heat recoverable members are inserted.

16. A method according to claim 10 wherein the heat recoverable member comprising a bilayer laminate having a recovery temperature in which a first layer is unidirectionally expanded and which tends to recover to its unexpanded state when heated to or above the recovery temperature and in which a second layer resists recovery of the first layer at or above the recovery temperature.

17. A method according to claim 16 wherein heating the bilayer laminate to or above its recovery temperature cause the laminate to recover involutely.

18. A method according to claim 17 wherein the duration of heating is less than the duration which would permit full shape recovery of the laminate.

19. A method according to claim 16 wherein, prior to recovery, the laminate has a generally planar construction and bends involutely when heated at or above its recovery temperature to a configuration in which the laminate has a curved surface.

20. A method according to claim 19 wherein a curved portion of the surface of the laminate exerts the pressure on the longitudinal ciliary muscle.

* * * * *